(12) United States Patent
Hancock

(10) Patent No.: US 7,585,282 B2
(45) Date of Patent: *Sep. 8, 2009

(54) SINGLE-HANDED BIOPSY SYSTEM

(75) Inventor: John Phillip Hancock, Fishers, IN (US)

(73) Assignee: Promex Technologies, Franklin, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/801,656

(22) Filed: May 10, 2007

(65) Prior Publication Data

US 2007/0213635 A1 Sep. 13, 2007

Related U.S. Application Data

(63) Continuation of application No. 10/776,750, filed on Feb. 11, 2004, now Pat. No. 7,229,419.

(60) Provisional application No. 60/446,745, filed on Feb. 11, 2003, provisional application No. 60/447,235, filed on Feb. 12, 2003.

(51) Int. Cl.
*A61B 10/00* (2006.01)
(52) U.S. Cl. .................................... 600/567
(58) Field of Classification Search ......... 600/564–567; 606/167, 170
See application file for complete search history.

(56) References Cited

U.S. PATENT DOCUMENTS

| 4,699,154 | A | 10/1987 | Lindgren |
| 4,944,308 | A | 7/1990 | Akerfeldt |
| 5,284,156 | A | 2/1994 | Schramm et al. |
| 5,476,101 | A | 12/1995 | Schramm et al. |
| 5,752,923 | A * | 5/1998 | Terwilliger .................. 600/562 |
| 6,126,617 | A * | 10/2000 | Weilandt et al. ............. 600/567 |
| 6,221,030 | B1 | 4/2001 | Avaltroni |
| 7,041,065 | B2 | 5/2006 | Weilandt et al. |
| 7,229,419 | B2 * | 6/2007 | Hancock ...................... 600/567 |
| 2002/0120212 | A1 * | 8/2002 | Ritchart et al. .............. 600/567 |
| 2004/0158172 | A1 | 8/2004 | Hancock |

* cited by examiner

*Primary Examiner*—Max Hindenburg
*Assistant Examiner*—Brian Szmal
(74) *Attorney, Agent, or Firm*—Maginot, Moore & Beck

(57) ABSTRACT

An automatic tissue sampling apparatus for use with a biopsy needle set includes a housing defining a cavity and a forward end opening for passage of an inner needle and outer cannula. Two carriers are slidably disposed within the cavity and are configured to support one of the inner needle and the outer cannula. Springs operably engage each carrier and have a cocked position to store potential energy and a firing position to releases the potential energy and drive the corresponding carrier toward the forward end of the housing. A single-handed cocking mechanism, operable to sequentially move the each driving mechanism to its respective cocked position, includes a manually operated cocking lever positioned outside the housing. A force transmission mechanism operably coupled between the cocking lever and the carriers is configured so that the force required to manually depress the cocking lever does not increase as the springs are compressed.

10 Claims, 22 Drawing Sheets

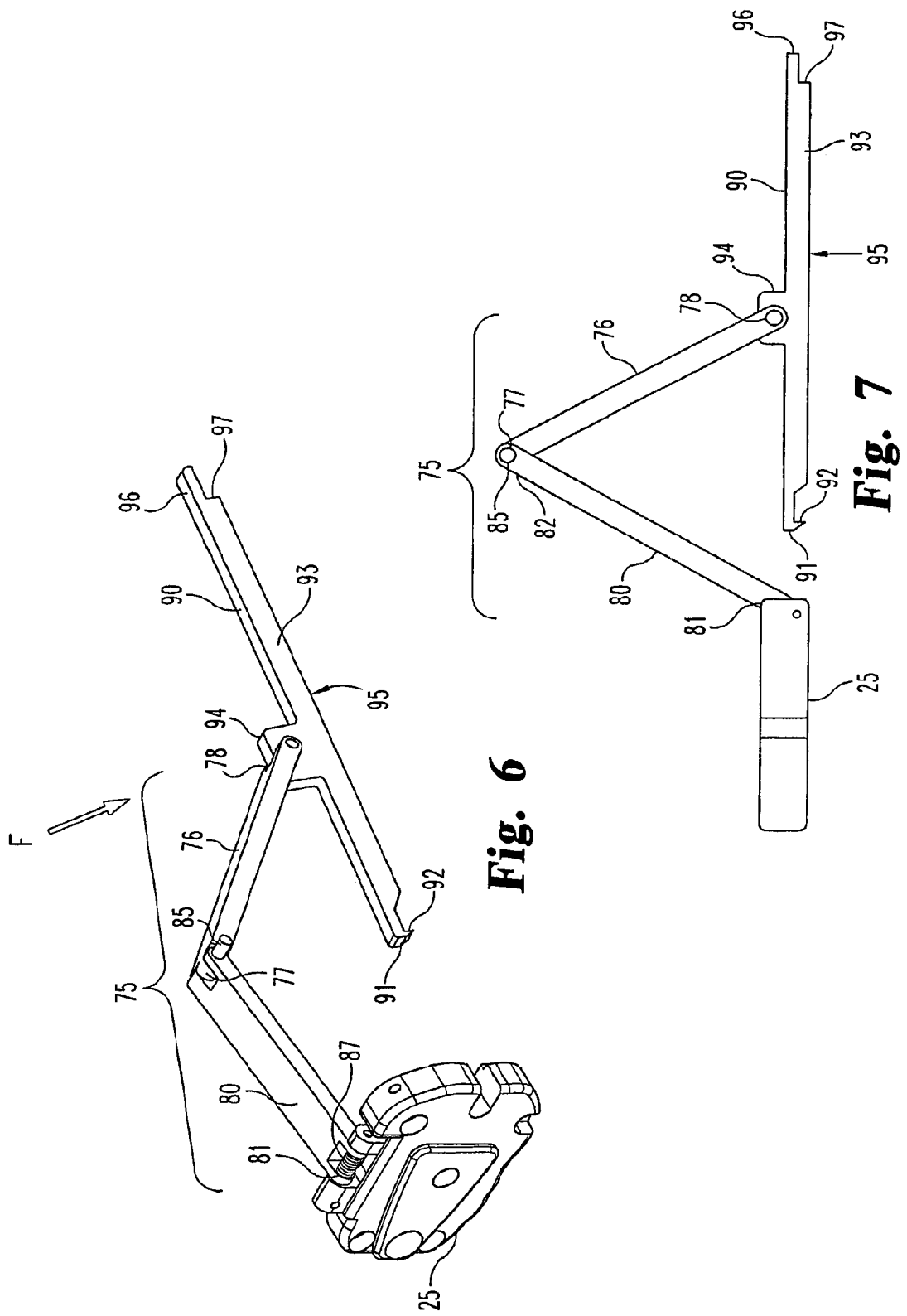

SINGLE-HANDED BIOPSY SYSTEM

This application is a continuation of application Ser. No. 10/776,750, filed on Feb. 11, 2004, which issued on Jun. 12, 2007, as U.S. Pat. No. 7,229,419, and which claims priority to Provisional application 60/446,745 filed Feb. 11, 2003 entitled BIOPSY DEVICE and to Provisional application 60/447,235 filed Feb. 12, 2003, entitled BIOPSY DEVICE.

BACKGROUND OF THE INVENTION

The present invention generally relates to the field of tissue sampling and harvesting. The invention more specifically relates to biopsy guns and needles.

Examples of typical double action biopsy guns are described in U.S. Pat. Nos. 4,699,154; 4,944,308; 5,284,156 and 6,221,030. Prior art biopsy guns are well known and widely used, but they suffer from certain significant drawbacks. For example, know prior art double action biopsy guns require the use of two hands. This is unfortunate because the tissue sampling is typically performed under visualization, such as ultra sound. It would be convenient to have a free hand to operate the visualization equipment. Many devices also make a compromise between sample quality and cocking force. To achieve significant needle velocity, prior art devices have required significant cocking force. To reduce cocking force has meant poorer sample quality.

Therefore, a need remains for double action biopsy guns that can be cocked and fired using a single hand yet which reliably provide high quality tissue samples.

BRIEF DESCRIPTIONS OF DRAWINGS

FIG. 6 is a side perspective view of a cocking slider and a force transmission mechanism engaged to the forward end of a device according to one embodiment of this invention.

FIG. 7 is a side elevational view of the components shown in FIG. 6.

DETAILED DESCRIPTION

Figure 1:
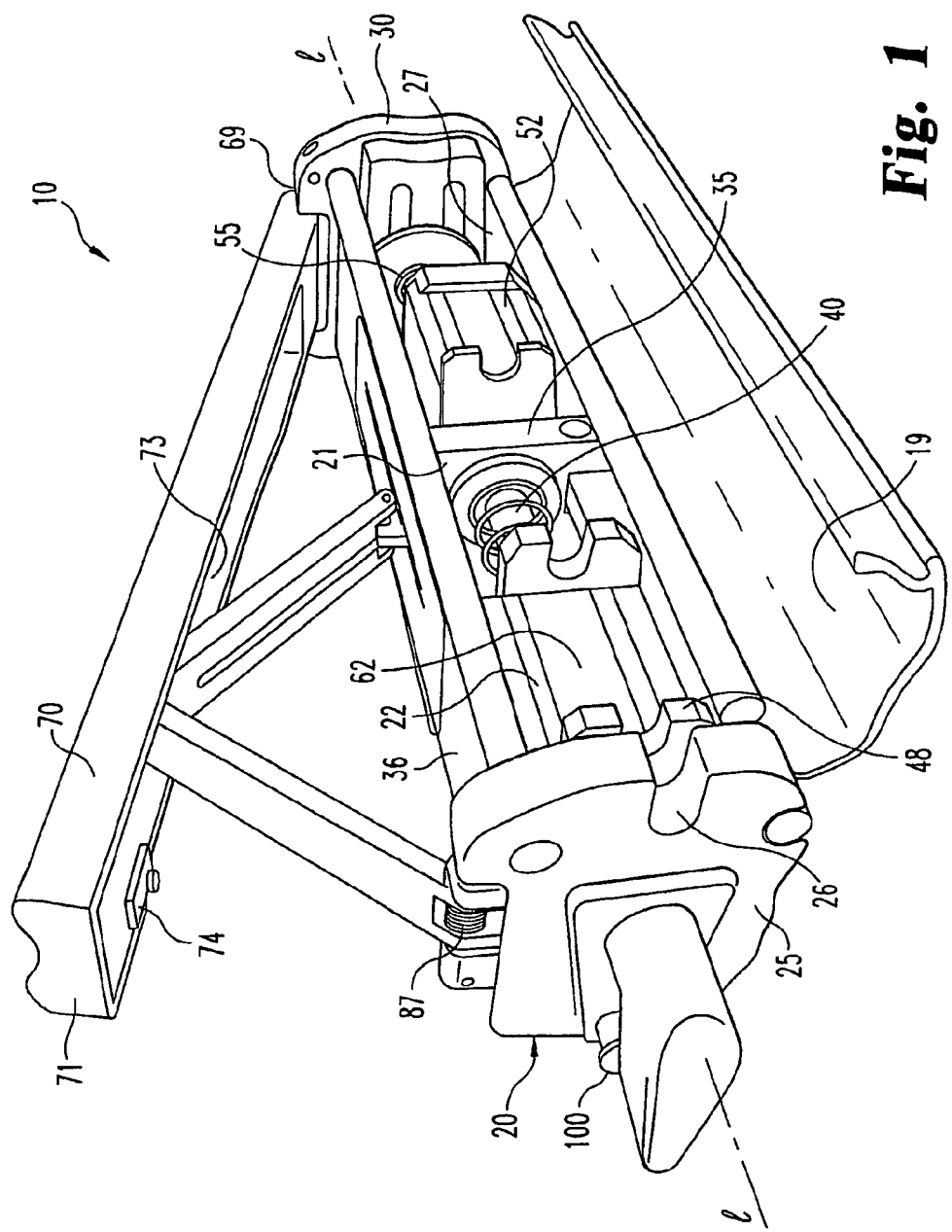
FIG. 1 is a side perspective view of a biopsy gun according to one embodiment of this invention.

For the purposes of promoting an understanding of the principles of the invention, reference will now be made to the embodiments illustrated in the drawings and specific language will be used to describe the same. It will nevertheless be understood that no limitation of the scope of the invention is thereby intended. The invention includes any alterations and further modifications in the illustrated devices and described methods and further applications of the principles of the invention that would normally occur to one skilled in the art to which the invention relates.

The present invention provides devices for automated tissue sampling. The devices of this invention can be operated with a single hand without compromising sample quality or efficiency.

FIG. 1 shows a biopsy gun 10 according to one embodiment of this invention. The biopsy gun 10 can be used with coaxial core biopsy needle sets, which are commercially available from US Biopsy, 3049 Hudson Street, Franklin, Ind. 46131 (800-755-1671). The biopsy needle sets include an inner needle or stylet having a first hub disposed at one end and a cutting point disposed on an opposite end with a tissue holding notch positioned between the cutting point and the first hub. The inner needle is disposed within an outer cannula, which has a second hub at one end and a cutting point disposed at the opposite end.

Biopsy device 10 includes a housing 20 defining an interior cavity 21 and a cover 19. The interior cavity 21 includes a forward portion 22 adjacent a forward end of the housing 20, which defines an opening 26 in communication with the interior cavity 21 for passage of the needle set. The interior cavity 21 also includes a rearward portion 27 adjacent a rearward end 30 with a transverse wall 35 disposed between the forward region 22 and the rearward region 27. A rotatable center shaft 40 is disposed within the housing 20 along a longitudinal axis L of the housing 20.

Figure 2:
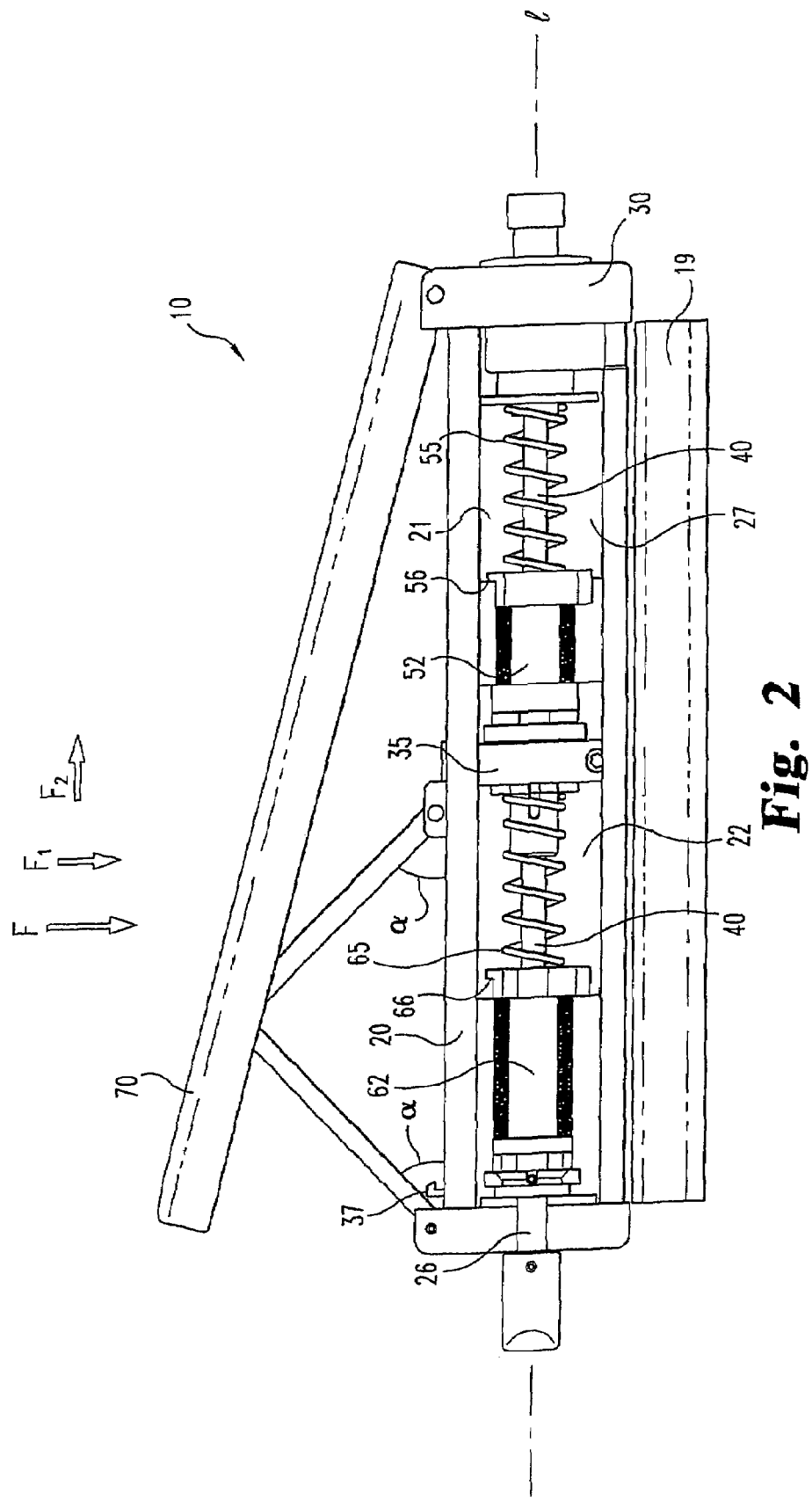
FIG. 2 is a side elevational view of the gun of FIG. 1 shown in the rest position.
Figure 3:
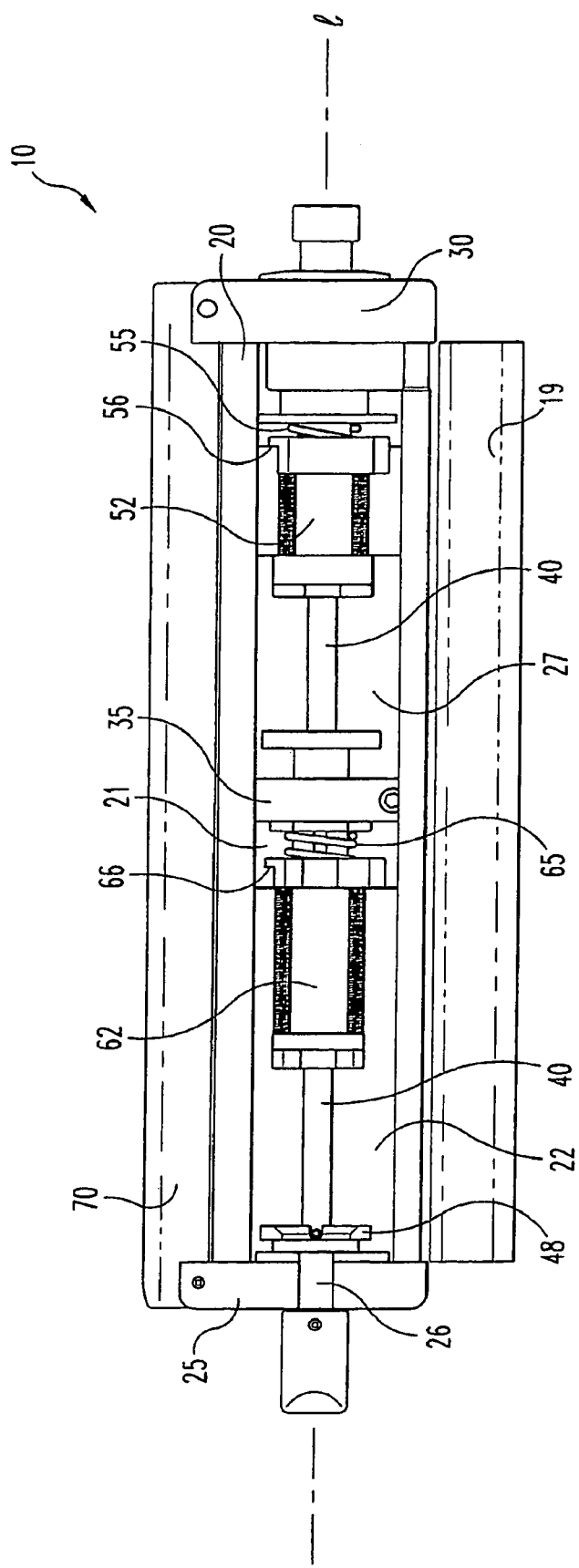
FIG. 3 is a side elevational view of the gun of FIG. 1 shown in the cocked position.
Figure 4:
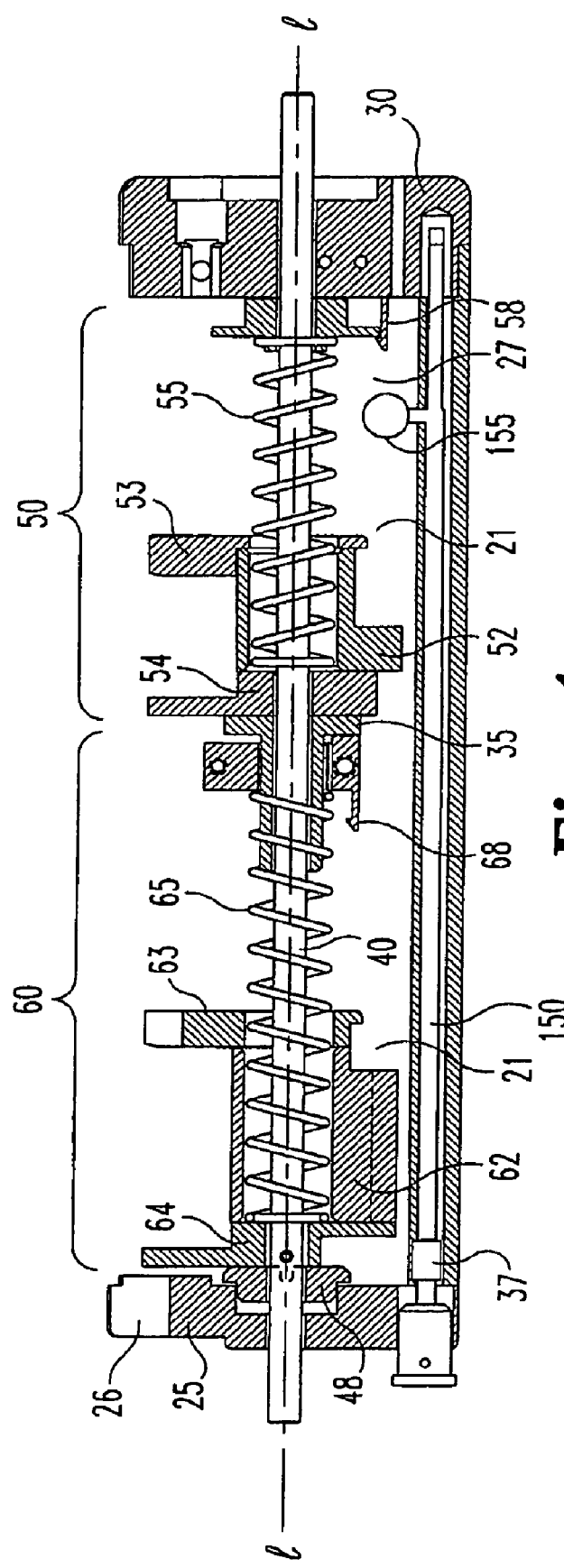
FIG. 4 is a longitudinal section of the view shown in FIG. 2.

Referring also now to FIGS. 2-4, the device 10 includes a rearward carrier assembly 50 configured to receive, support and carry one of the needle hubs. In one embodiment, the rearward assembly is configured to carry an inner stylet hub. The rearward carrier assembly 50 includes a rearward carrier 52, a rearward drive mechanism 55 and a rearward retaining member 58. The rearward carrier 52 has a hub support portion 54 and a rearward drive portion 53 mounted on the center shaft 40 in the rearward portion 27. The rearward carrier 52 is movable on the center shaft 40 along a path substantially parallel to the longitudinal axis L of the housing between a first resting position as shown in FIG. 2 and a first cocked position as shown in FIG. 3.

The rearward drive mechanism 55 is disposed within the interior cavity in operable engagement with the rearward carrier 52. The rearward drive mechanism 55 is movable between a cocked position in which the drive mechanism stores potential energy and a firing position in which the mechanism releases the potential energy to drive the rearward carrier 52 forward toward the forward end 25 of the housing 20. In one embodiment, the rearward drive mechanism includes a rear spring member 55. The rear spring member 55 is positioned within the rearward region 27 of the housing 20 and biases the rearward carrier 52 forwardly toward the first resting position. The rear spring member 55 is compressible to the cocked position.

The rearward retaining member 58 can be an L-shaped hook member biased upwardly with a leaf or other spring. The retaining member 58 is configured to releasably retain the rearward carrier 52 in the cocked position. The rearward retaining member 58 is releasable in response to a trigger 100 operatively engaged to the rearward retaining member 58.

The device 20 also includes a forward carrier assembly 60 configured to receive, support and carry the other one of the needle hubs. In one embodiment, the forward carrier is configured to carry an outer cannula hub. The forward carrier assembly 60 includes a forward carrier 62, a forward drive mechanism 65 and a forward retaining member 68. The forward carrier 62 has a hub support portion 64 and a forward drive portion 63 mounted on the center shaft 40 in the forward portion 22. The forward carrier 62 is movable on the center shaft 40 along a path substantially parallel to the longitudinal axis L of the housing between a second resting position as shown in FIG. 2 and a second cocked position as shown in FIG. 3.

The forward drive mechanism is disposed within the interior cavity 21 in operable engagement with the forward carrier 62. The forward drive mechanism is movable between a cocked position in which the drive mechanism stores potential energy and a firing position in which the mechanism releases the potential energy to drive the forward carrier 62 forward toward the forward end 25 of the housing 20. In some embodiments, the forward drive mechanism includes a front spring member 65. The front spring member 65 is positioned within the forward region 22 of the housing 20 and biases the forward carrier 62 forwardly toward the second resting position. The front spring member 65 is compressible to the cocked position.

The forward retaining member 68 is configured to releasably retain the forward carrier 62 in the second cocked position. The forward retaining member 68 is releasable in response to the rearward carrier 52 moving from the first cocked position to the first resting position.

The hub support portions 54, 64 of both of the carriers 52, 62 can be equipped with desirable features, such as those that will support and maintain the hubs in a desired relationship by preventing rotation, for example. Other such suitable features are contemplated by this invention.

The device 10 includes a cocking mechanism operable to sequentially move the driving mechanisms to the corresponding cocked positions. In some embodiments, the cocking mechanism is a two stage cocking assembly that moves one of the carriers to the corresponding cocked position with a first actuation of the cocking assembly and then moves the other of the carriers to the corresponding cocked position with a second actuation of the cocking assembly.

The cocking mechanism includes a manually operated cocking lever 70 positioned outside the housing 20 for single handed manipulation while holding the housing. Referring again to FIGS. 1 and 2, the cocking lever 70 is pivotally mounted to the housing 20 at a point 69 and can be manually depressed against the housing 20. The cocking lever 70 is disposed externally on a lever wall 36 of the housing 20. In one specific embodiment, the lever wall 36 is disposed between the forward end 25 and the rearward end 30 of the housing 20 and the cocking lever 70 is laterally supported from the lever wall 36.

The cocking mechanism includes a force transmission mechanism operably coupled between the cocking lever 70 and each of the carriers 52, 62. Due to the force transmission mechanism of this invention, the force required to manually depress the cocking lever 70 to compress each of the forward and rear springs 65, 55 does not increase as the spring is compressed. The lever has a declining operator force requirement that compensates for the increasing force required to further compress each spring. The lateral position of the lever 70 and the declining operating force allow single-handed use of the device without compromising spring force and sample quality.

Referring now to FIGS. 6 and 7, in some embodiments, the cocking assembly also includes a cocking slider 90 having an elongated bar portion 93. The slider 90 is movable along a path in response to actuation of the cocking lever by action of the force transmission mechanism.

The cocking slider 90 includes a forward engagement member 92 at a forward end 91 releasably engageable to an engagement portion 66 (FIG. 2) on the forward carrier 62. A rearward engagement member 97 is also provided at a rearward end 96 of the slider 90, which is releasably engageable to an engagement portion 56 (FIG. 2) on the rearward carrier 52. In a specific embodiment, the forward engagement member 92 is shaped as a hook configured to drag the forward carrier 62 back to the cocked position. The rearward engagement member 97 can be shaped as a notch to serve as a pusher element as shown in FIG. 6 to push the rearward carrier 52 back to the cocked position. In other specific embodiments, the cocking slider 90 includes a beam-cocking slider connector 94 forward of the center 95 of the elongated bar 93.

As shown in FIGS. 8-13, the cocking slider 90 has a length sufficient to span a distance between the forward carrier 62 and the rearward carrier 52. The cocking slider 90 is slidably disposed within the housing 20 so that when the cocking slider 90 slides in a rearward direction R away from the forward end 25 of the housing 20 and an engagement portion 92, 97 applies a force against one of the carriers 52, 62, the carrier is moved to its cocked position.

Referring again also to FIGS. 6 and 7, the force transmission mechanism 75 is engaged between the cocking lever and the cocking slider. The mechanism 75 translates the pivoting movement of the cocking lever 70 to the sliding movement of the cocking slider 90 in the rearward direction R against the carriers 52, 62. The force transmission mechanism includes an elongated rearward beam 76 pivotally connected at a first end 78 to the slider 90 and slidably supported at an opposite end 77 by the cocking lever 70. In one specific embodiment, the beam 76 is connected to the beam-slide connector 94 of the slider 90. A forward beam 80 is pivotally connected at one end 81 to the housing 20. In one specific embodiment, the forward beam is engaged to the forward end 25 of the housing 20. A beam bearing 85 is slidably supported by the cocking lever 70 and pivotally connects the ends 77, 82 of the beams 76, 80.

The force transmission mechanism 75 also includes a biasing element 87 at the one end 81 of the forward beam 80. The biasing element 87 biases the beam away from the housing 20, which in turn pivots the cocking lever 70 away from the housing 20 when the cocking lever 70 is not latched.

The cocking slider 90 is disposed between the cocking beams 76, 80 and the carriers 52, 62 to transmit force From the lever 70 to the beams 76, 80 to the carriers 52, 62 to move the carriers 52, 62 from the corresponding resting position to the corresponding cocked position. Referring again to FIG. 2, each of the cocking beams 76, 80 form an angle α with the lever wall 36 of the housing 20. The beam bearing 85 is movable against the cocking lever 70 between a lever open position with the cocking beams 76, 80 in a retracted position (FIG. 2) and a lever closed position with the cocking beams 76, 80 in an extended position (FIG. 3). The angle α is smaller when the cocking beams 76, 80 are in the extended position relative to when the cocking beams 76, 80 are in the retracted position. In a specific embodiment, angle α is approximately 45.degree. in the retracted position. Therefore, applying a force F on the lever transmits roughly half of the force in the direction of arrow $F_1$ and half of the force in the direction of arrow $F_2$. As angle α decreases, a mechanical advantage is achieved as more of the force F is applied in the direction of arrow $F_2$, which makes closing the lever easier. However, as the spring 55, 65 compresses, it requires more force to continue compression. The declining force requirement on the lever 70 makes the increased force requirement of the spring transparent to the user.

Figure 8:
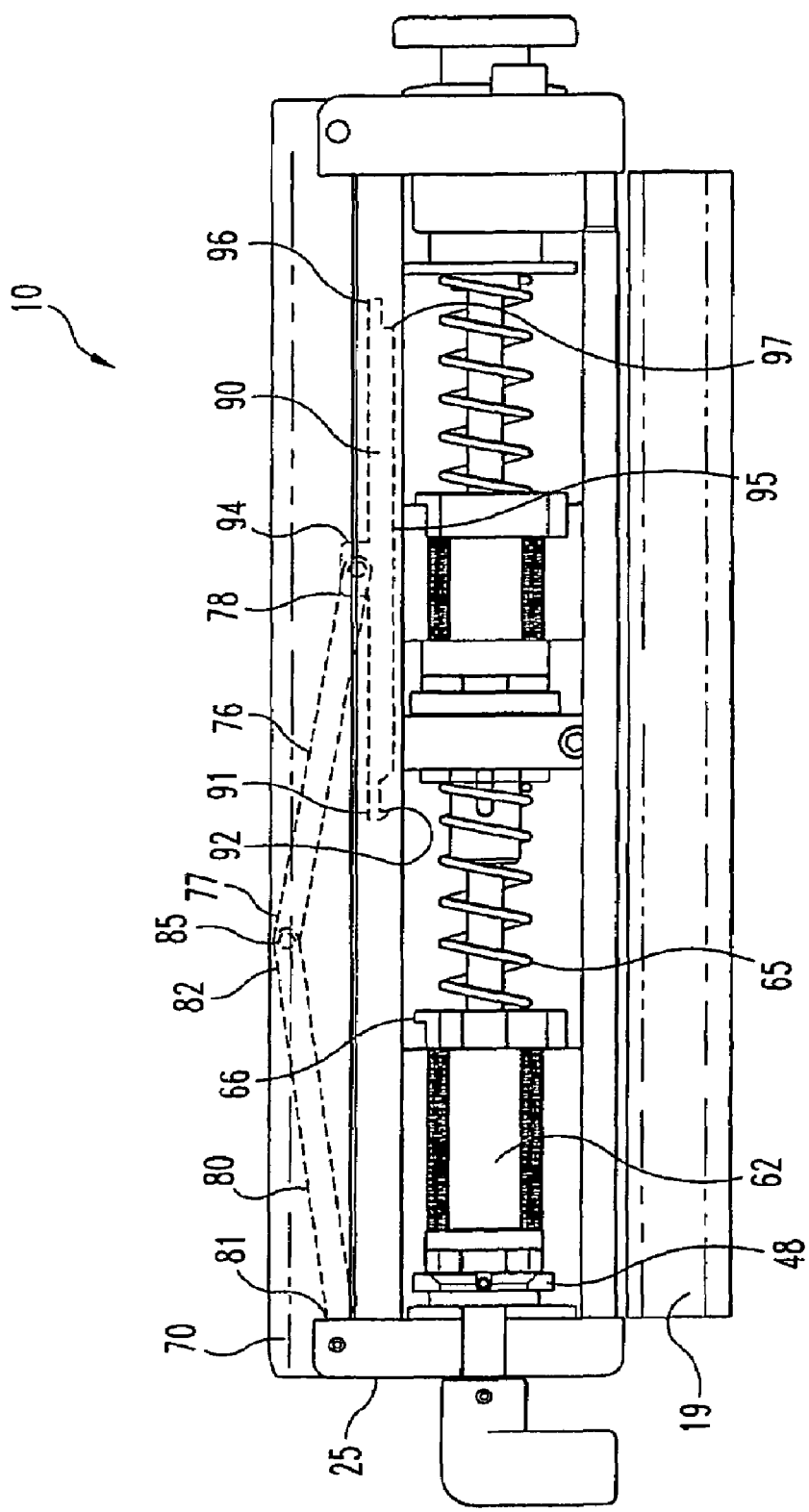
FIG. 8-13 are partial side sectional views of a device shown moving through the cocking and firing sequence according to one embodiment of this invention.
Figure 9:
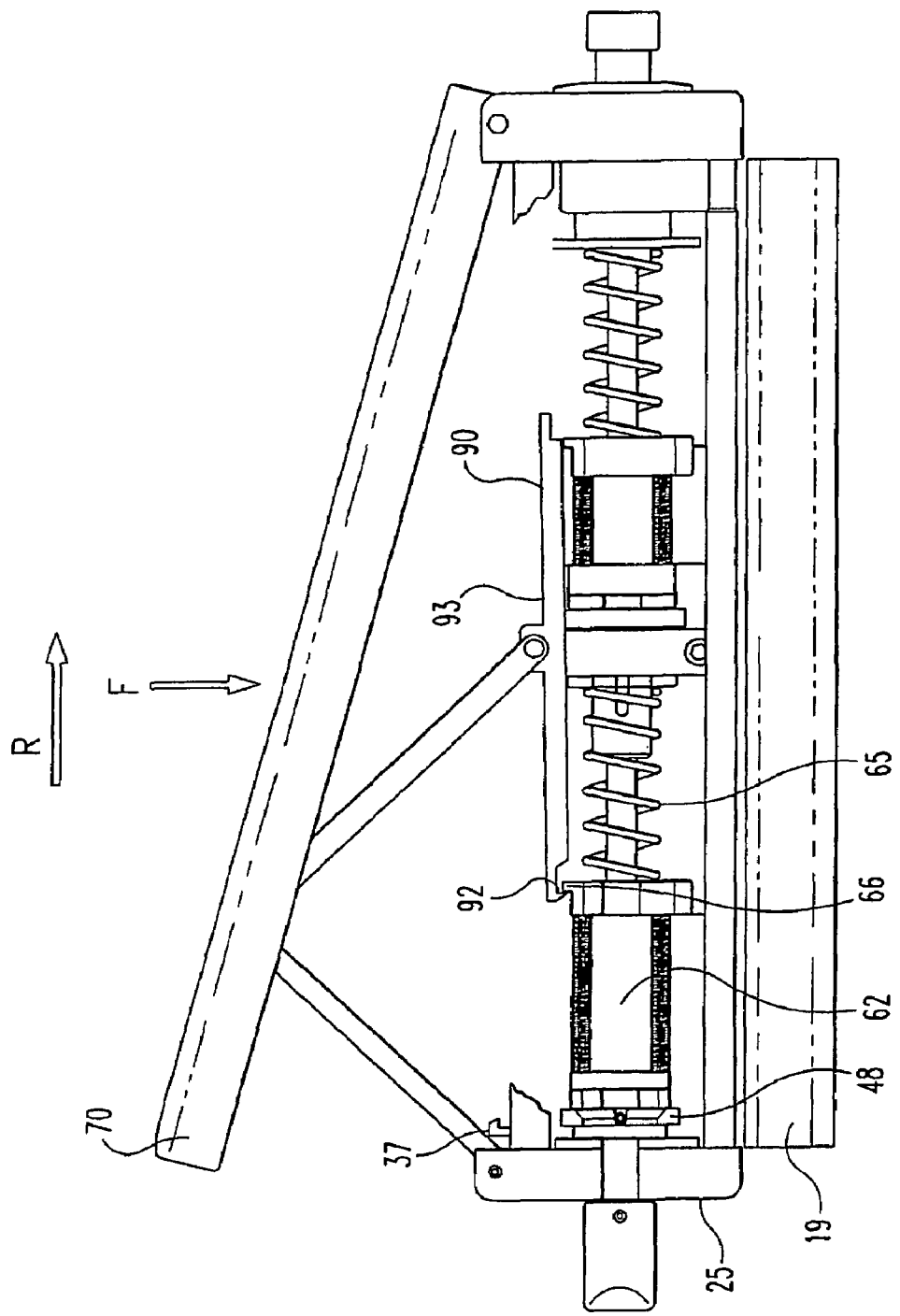
Figure 10:
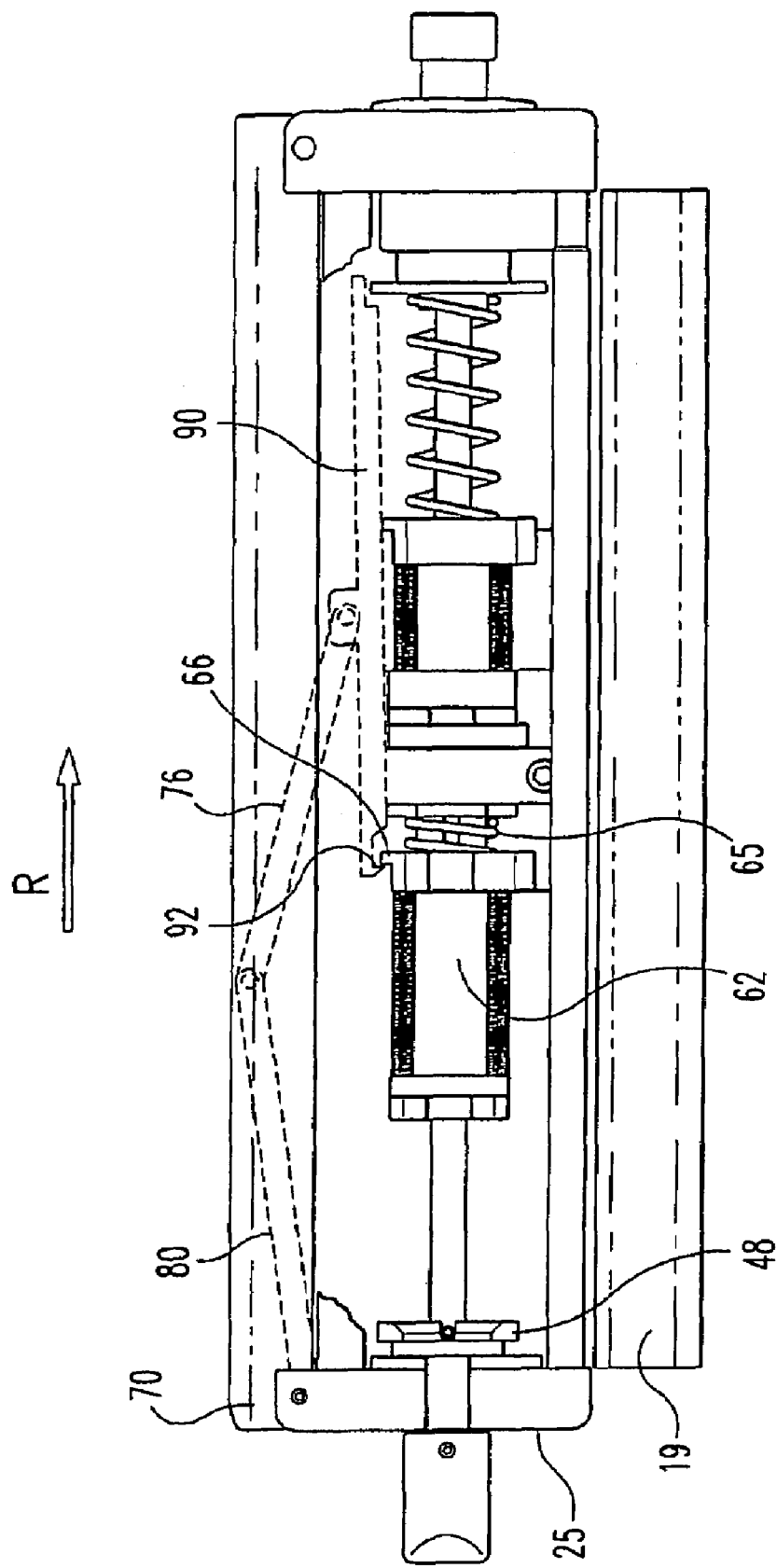
Figure 11:
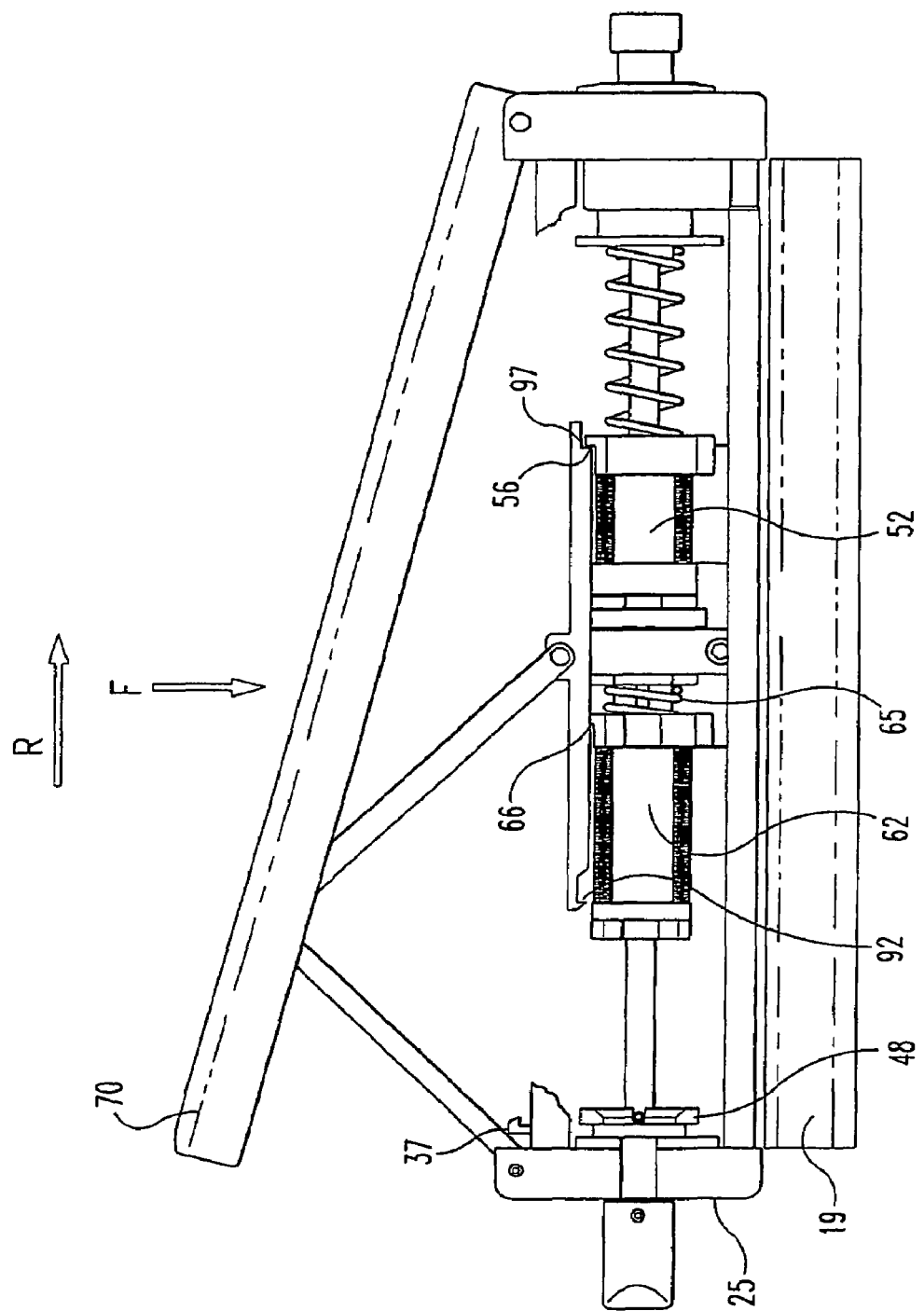

The operation of one embodiment of the force transmission mechanism 75 and the cocking slider 90 is shown in FIGS. 8-13. In FIG. 8, the device 10 is shown in a resting state with the safety off and the cover 19 open. The safety is then turned to the safety-on position, which prevents actuation of the trigger. In the safety-on position, the cocking lever 70 is unlatched and opens as shown in FIG. 9. As the cocking lever 70 swings open, the cocking slider 90 moves forward so that the forward engagement member 92 is aligned with the forward carrier engagement portion. Upon actuation of the cocking lever 70, force F is applied to the bar 93 at the beam-slider connector 94. Because the connector 94 is forward of the center 95 of the slider bar 93 and the rearward end 96 of the slider 90 rests on the engagement portion 56 of the rearward carrier 52, the forward end 91 of the slider tips toward the forward carrier 62 to engage the forward engagement member 92 with the forward carrier 62. As the cocking lever is closed, the slider 90 is forced backward and drags the forward carrier to the cocked position against the bias of the spring 65 as shown in FIG. 10.

When the force F is released, the cocking lever 70 swings open again and the slider 90 slides to the forward position (FIG. 11) with the rearward engagement member 97 aligned with the rearward carrier engagement portion 56. This time, when the force F is applied, the slider 90 is prevented from tilting in the forward direction by the presence of the forward carrier 62, and the slider tilts towards the rearward carrier 52, engages and pushes the rearward carrier 52 back to the cocked position.

Figure 12:
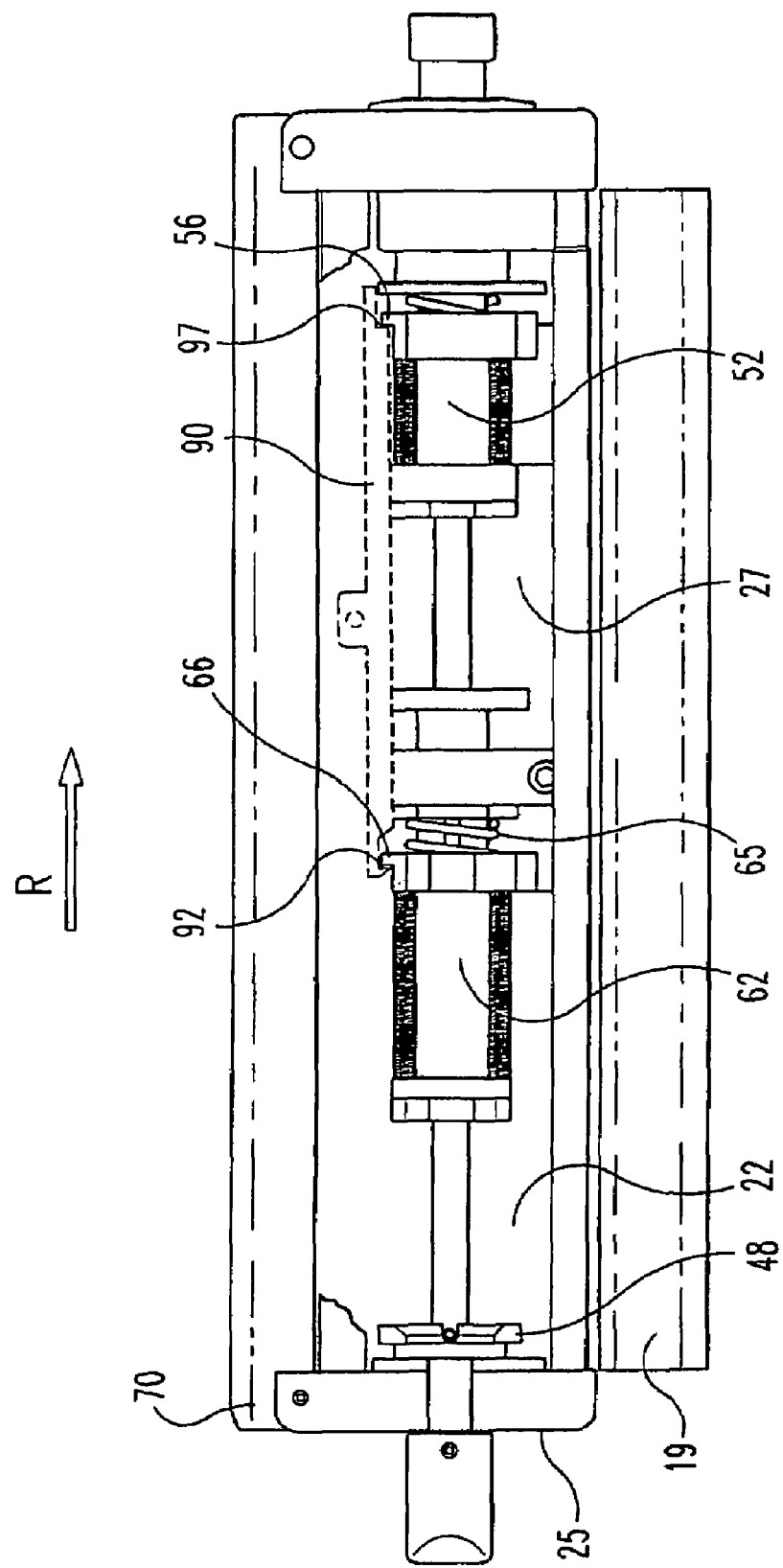

The fully cocked configuration is shown in FIG. 12. At this step, the gun cannot fire because the safety mechanism prevents the actuation of the trigger. In addition, the slider 90 may still be engaged to one or both of the cannula carriers 52, 62.

Figure 14:
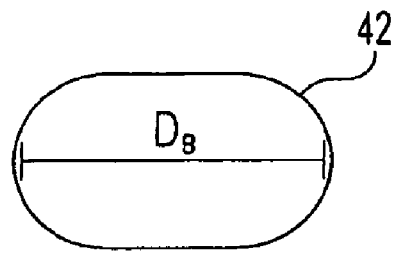
FIG. 14 shows the shape of the rear cam plate.
Figure 15:
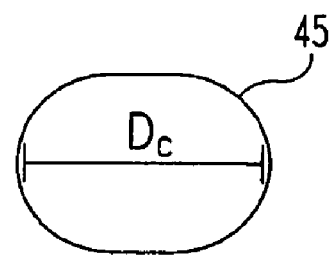
FIG. 15 shows the shape of the center cam plate.
Figure 16:
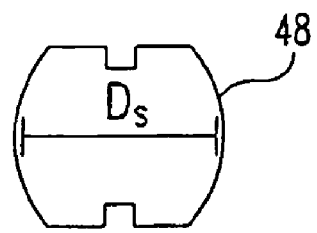
FIG. 16 is an elevational view of the front safety cam.
Figure 17:
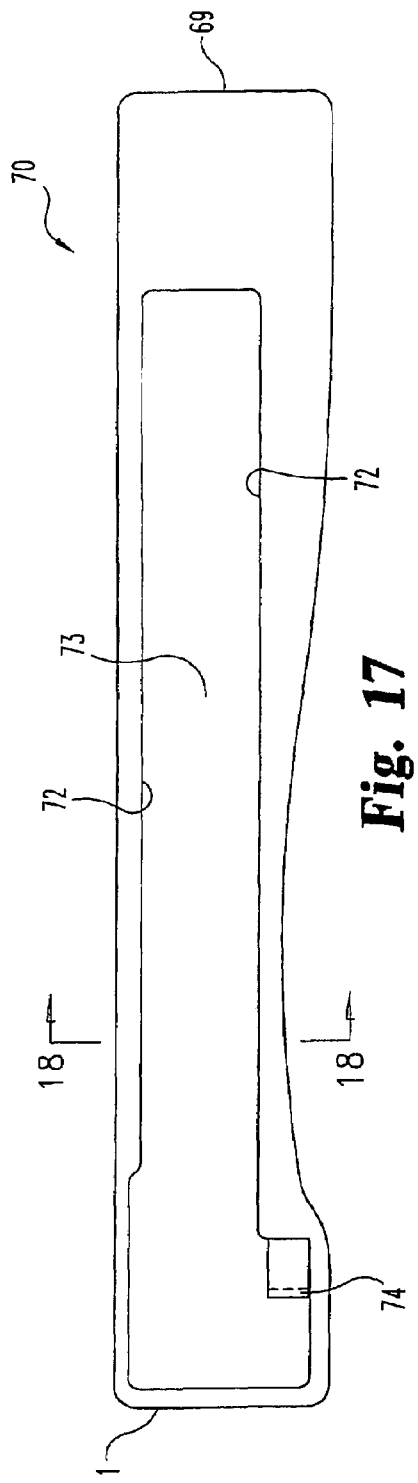
FIG. 17 is an elevational view of the internal surface of the cocking lever according to one embodiment of this invention.
Figure 18:
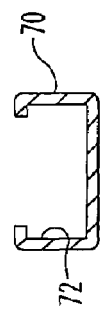
FIG. 18 is a cross sectional view taken along lines 18-18 of the cocking lever shown in FIG. 17.
Figure 19:
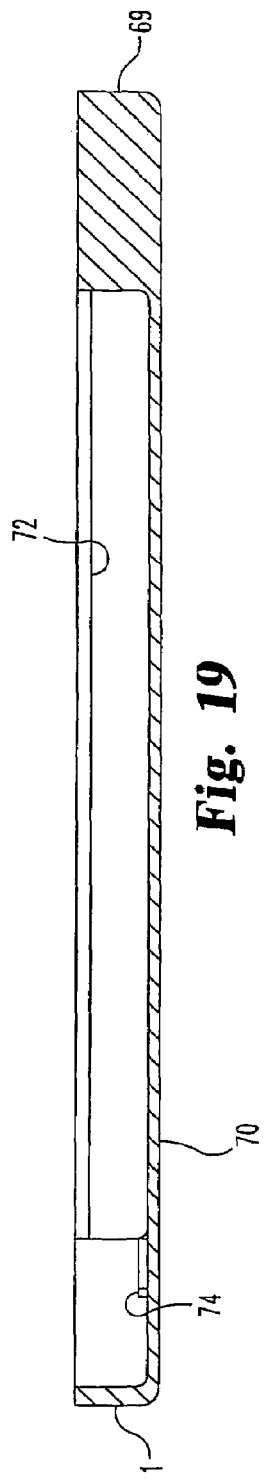
FIG. 19 is a longitudinal sectional view of the cocking lever shown in FIG. 17.

Rotating the safety allows the trigger to be actuated. In some embodiments, rotating one of the safety knobs rotates a cam that pushes the slider 90 up and away from the carriers 52, 62. In the embodiment shown in FIG. 13, a back elliptical plate 42 (FIG. 14) and a center elliptical plate 45 (FIG. 15) rotate with the rotatable shaft 40. Both the back and center elliptical plates 42, 45 have a major dimension $D_B$, $D_C$ sufficient to push the slider 90 from the position shown in FIG. 12 to the position shown in FIG. 13.

Figure 13:
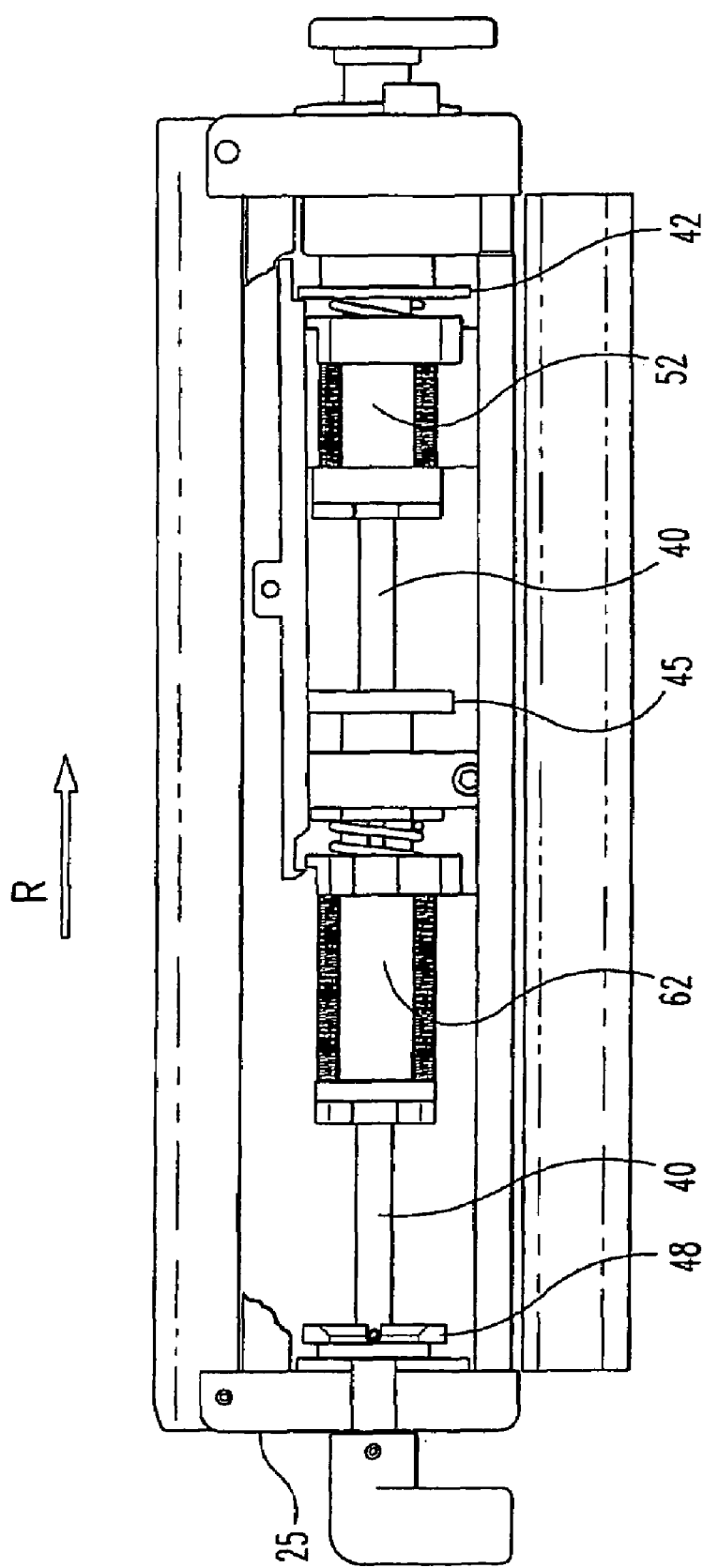

The device 10 shown in FIG. 13 is now ready to fire. Once the device is fired, it returns to the configuration shown in FIG. 8.

Therefore, upon actuation of the cocking lever 70, the forward end 91 of the slider 90 tips toward the forward carrier 62 when the forward carrier 62 is in the resting position, and alternately, the forward end 91 rests upon the forward carrier 62 and the rearward end 96 tips towards the rearward carrier 52 to align the rearward engagement member 97 with the rearward carrier 52 when the forward carrier 62 is in the cocked position.

Figure 20:
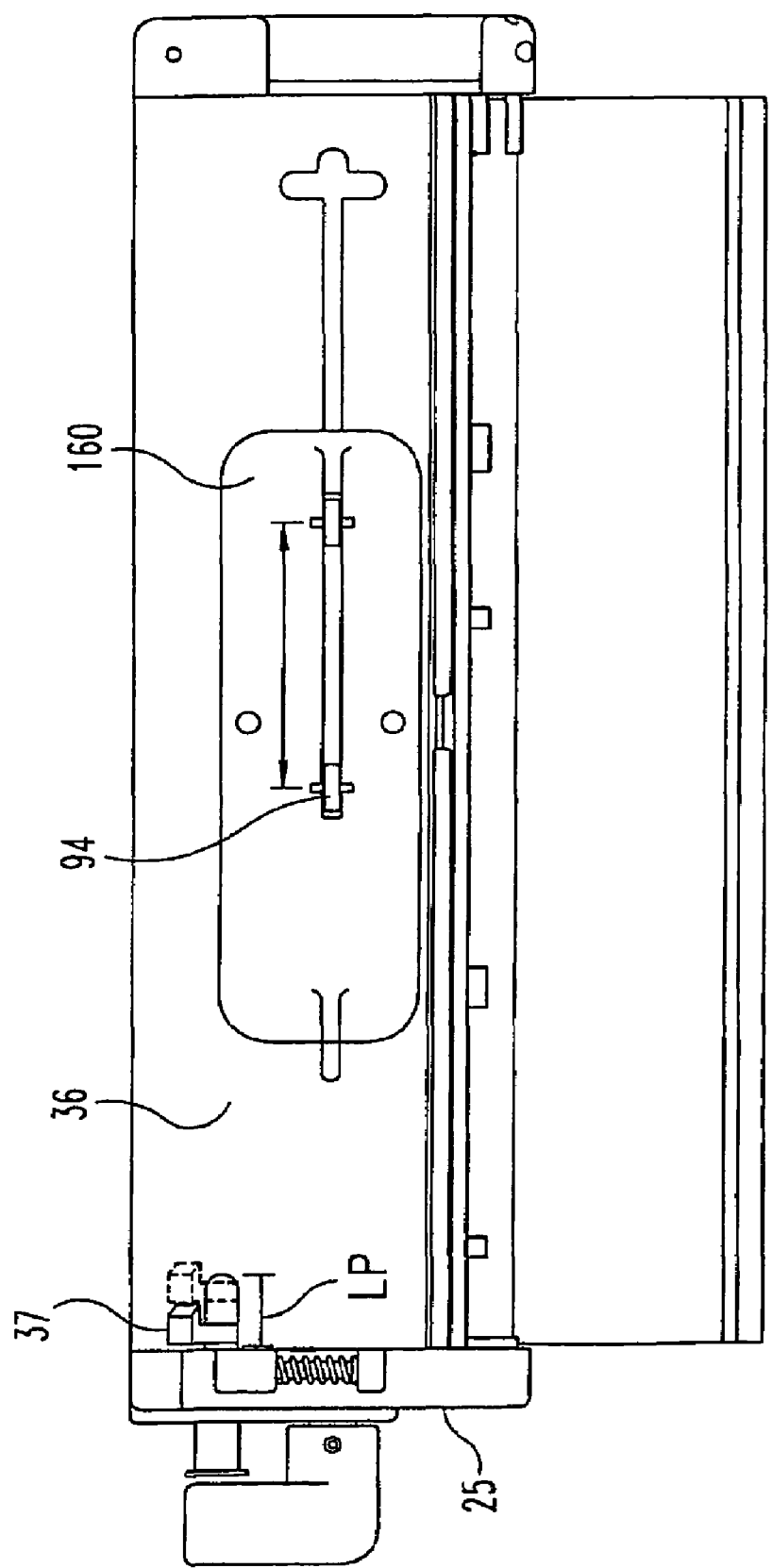
FIG. 20 is a side elevational view of device according to one embodiment of this invention showing details of the lever wall of the housing.

Details of the cocking lever are shown in FIGS. 1, 12 and 17-19. In this specific embodiment, the cocking lever 70 defines a recess 73 for receiving the force transmission mechanism 75 and a groove 72 running parallel to the longitudinal axis L of the housing 20. The groove 72 receives the beam bearing 85 in sliding engagement. A lever hook 74 is disposed on the cocking lever 70 for engaging a lever latch 37, which projects from the lever wall 36. Referring now to FIG. 20, the lever latch 37 is movable along a lever latch path LP between an engaged position adjacent the forward end 25 and a released position towards the rearward end 30.

In this particular embodiment, the latch mechanism includes a safety cam 48 rotatable in response to rotation of one of the safety knobs 130, 140. The safety cam 48 has a major dimension Ds sufficient to block movement of the lever latch 37 along the latch path LP from the engaged position to the released position.

Figure 5:
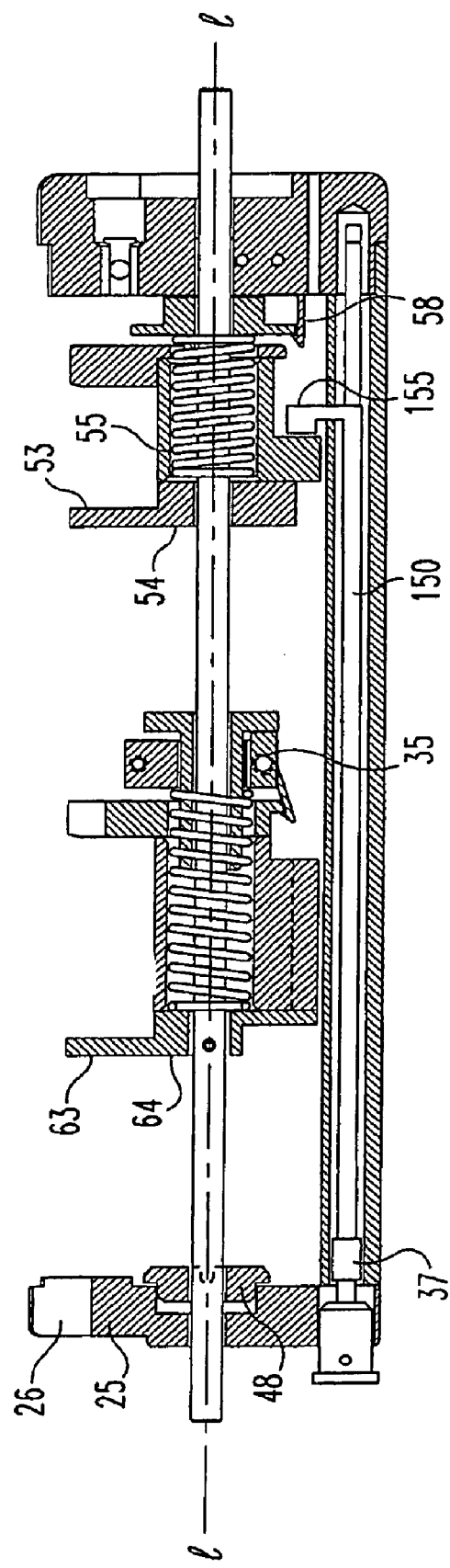
FIG. 5 is a longitudinal section of the view shown in FIG. 3.
Figure 21:
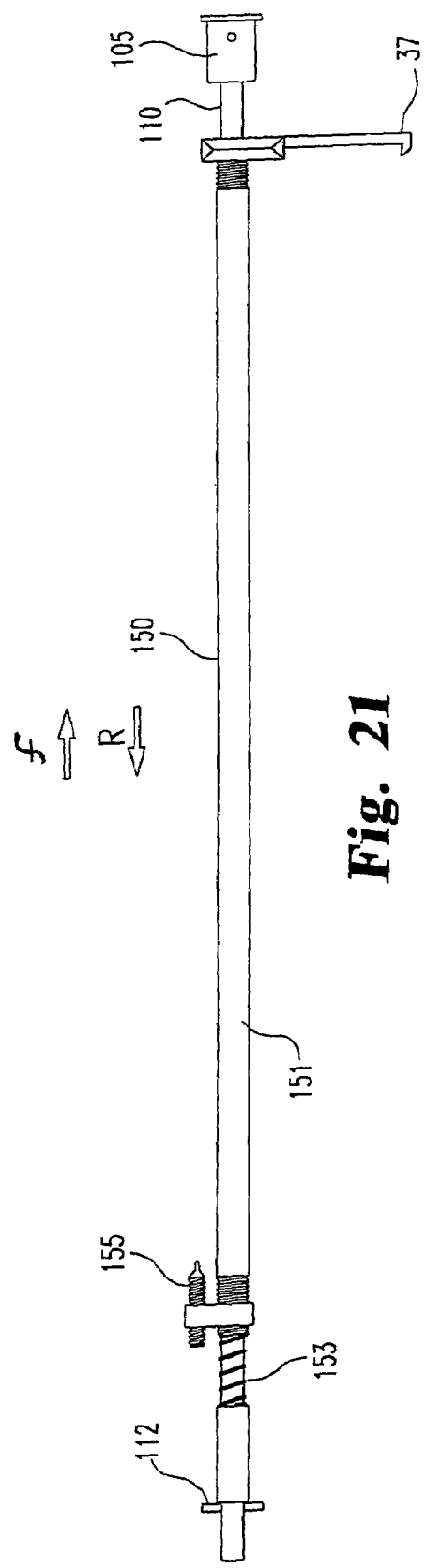
FIG. 21 is a side elevational view of the latch linker and the trigger linker mechanisms of one embodiment of this invention.
Figure 22:
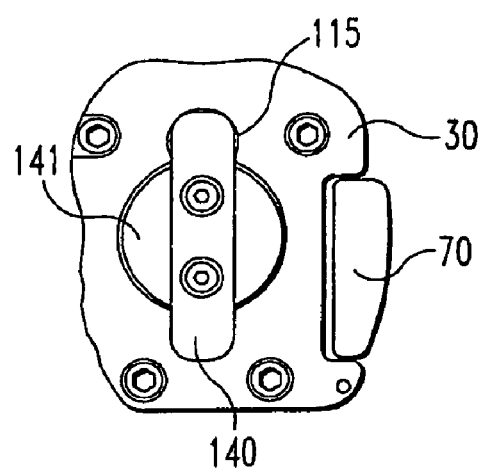
FIG. 22 is an elevational view of the rearward end of a gun according to one embodiment with the safety in the on position.
Figure 23:
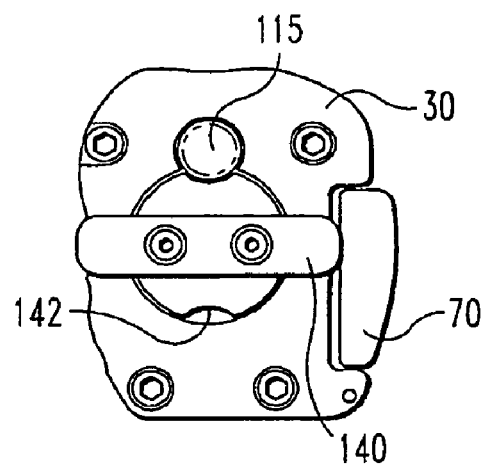
FIG. 23 is an elevational view of the rearward end of the gun shown in FIG. 22 with the safety in the off position.
Figure 24:
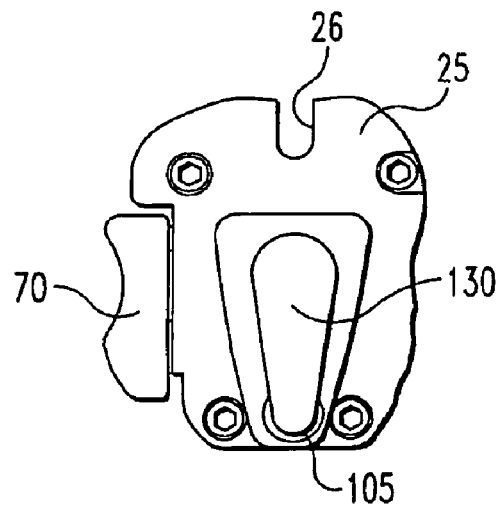
FIG. 24 is an elevational view of the forward end of the gun shown in FIG. 22 with the safety in the on position.
Figure 25:
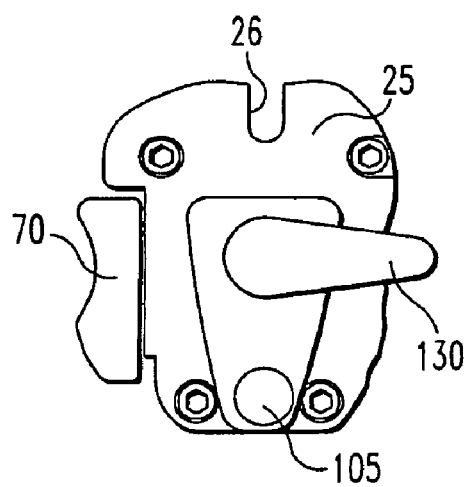
FIG. 25 is an elevational view of the forward end of the gun shown in FIG. 22 with the safety in the off position.

Referring also now to FIGS. 4, 5 and 21, some embodiments provide an elongated lever latch linker 150 positioned parallel to the longitudinal axis L. The lever latch linker 150 operably connects the lever latch 37 to a lever latch pusher 155 disposed in the rearward portion 27 of the housing. In one specific embodiment, the linker 150 includes a hollow tube 151. The lever latch linker 150 is preferably biased in the forward direction along arrow F so that the lever latch is biased in the forward direction f to disengage the lever hook 74. The linker 150 is movable in the rearward direction R in response to movement of the rearward carrier 52 to the first cocked position. When the rearward carrier 52 is in the cocked position, the lever latch pusher 155 is pushed in the rearward direction, which holds the latch 37 in the engaged position. Therefore, when the rearward carrier 52 is in the cocked position, the lever latch 37 is engaged to the lever hook 74 and the cocking lever 70 is closed against the lever wall 36.

Figure 26:
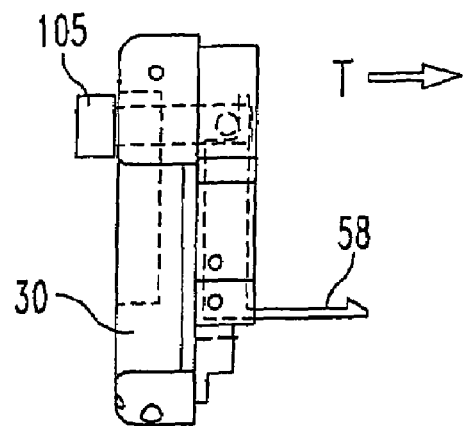
FIG. 26 is a side elevational view of the rearward end of the device of FIG. 22.
Figure 27:
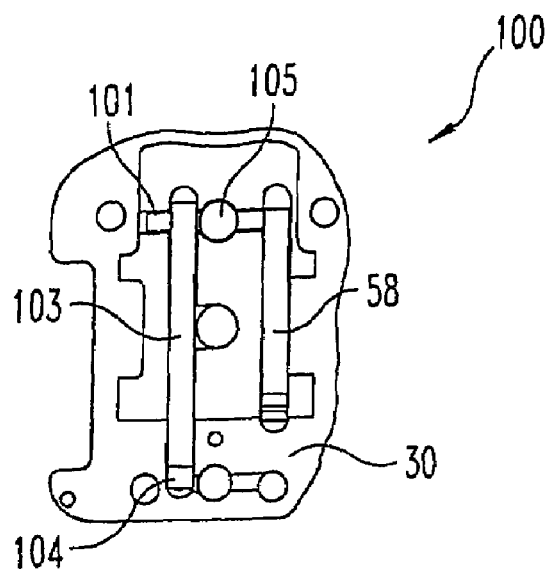
FIG. 27 is an elevational view of the inside of the rearward end of the device of FIG. 22.

In one embodiment, the gun 10 has a front trigger button 105 and a rear trigger button 115. Both of the trigger buttons 105, 115 are operably engaged to the trigger mechanism 100 shown in FIG. 26. The trigger mechanism 100 includes trigger link bar 101 connected to the rearward retaining member 58 and a trigger actuator translator 103, which actuates the trigger mechanism when a force is applied to trigger actuator element 104. When the trigger link bar is pushed in the direction of arrow T, the rearward retaining member 58 is tilted and releases the rearward carrier 52.

Referring again to FIG. 21 the front trigger button 105 is operably linked to the rear trigger button 115 by an elongated trigger link 110. The trigger link 110 is a solid rod, which is coaxially disposed within the lever latch link 150 in one specific embodiment. Pressing the front trigger button 105 causes the trigger link actuator 112 of the trigger link 110 to press the trigger actuator element 104 of the trigger mechanism 100.

The trigger mechanism is automatically blocked by rotating one of the safety knobs 130, 140 to release the cocking lever 70 as discussed above. The safety knobs may physically block access to the trigger buttons, although this is not necessary. In one embodiment, the safety knob 140 includes a flattened skirt member 141 that slides under trigger button 115 to prevent depression of the button. The trigger can be actuated when the safety knob is rotated so that the recess 142 is aligned with the trigger button 115.

Figure 28:
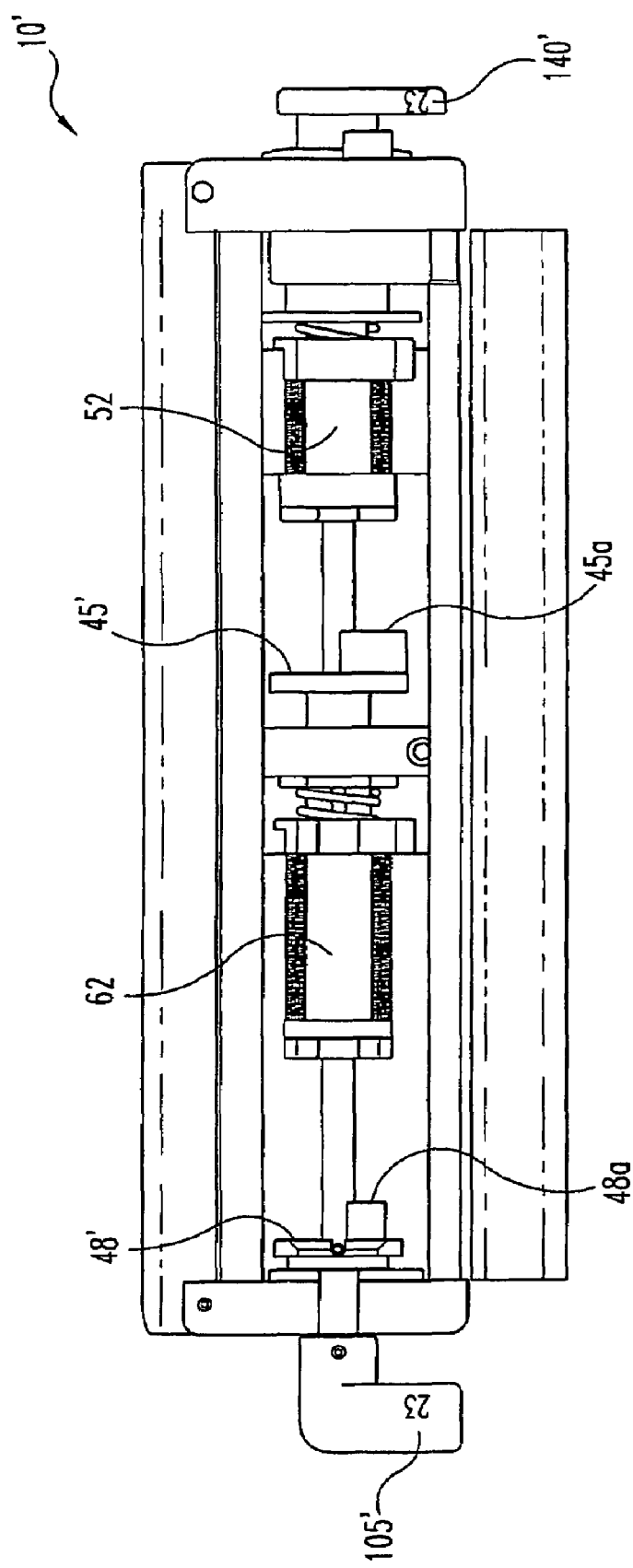
FIG. 28 is a side elevational view of another embodiment of the present invention.
Figure 29:
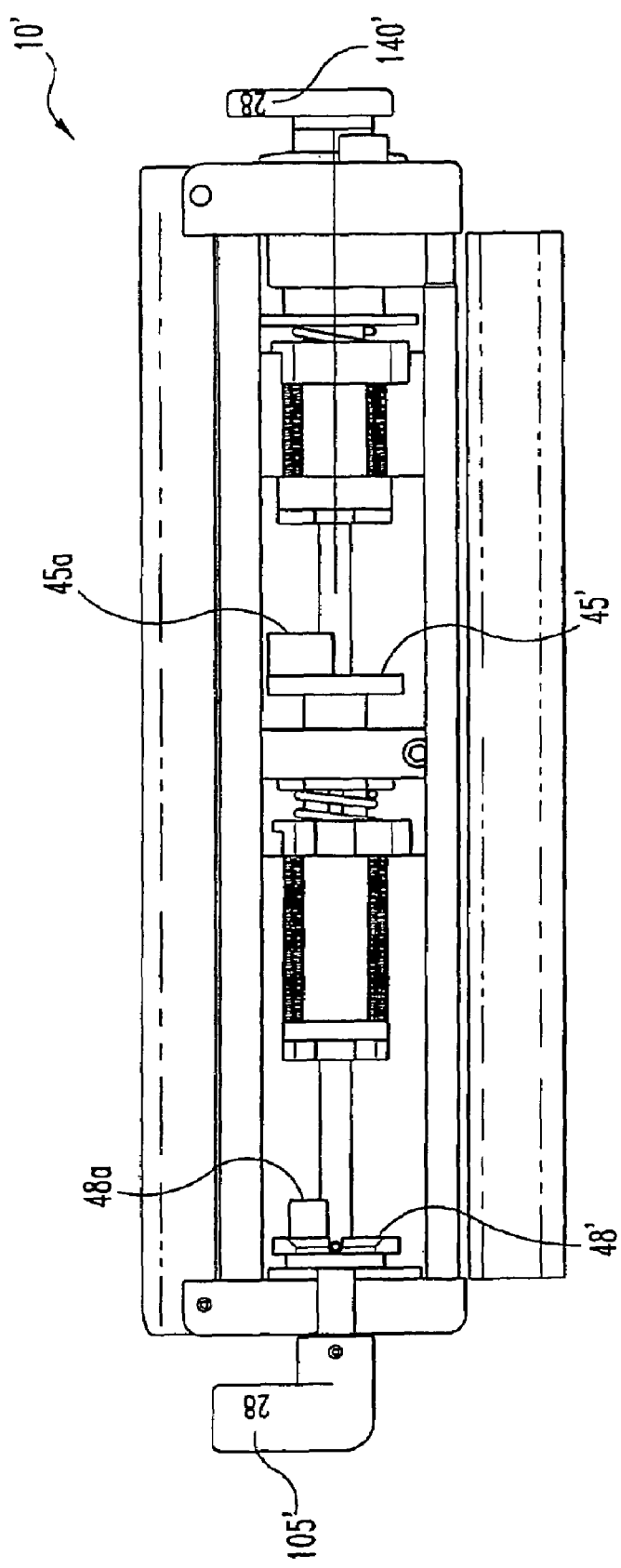
FIG. 29 is a side elevational view of the device shown in FIG. 28 showing the device in another configuration.

In a certain embodiment depicted in FIGS. 28 and 29, the device 10' provides for variable stroke length of the needle set. The alternate stroke lengths are selected by turning one of the safety selector knobs 105', 140'. The safety cam 48' and the center elliptical stop 45' are each provided with a protrusion 45a, 48a that limit the travel of the carriers 62, 52, respectively when a shorter stroke length is selected. For the longer stroke length configuration, the carriers 62, 52 simply pass over the protrusions 45a, 48a.

Figure 30:
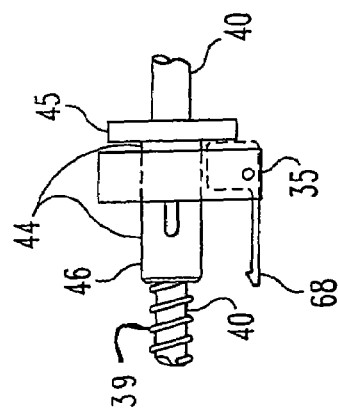
FIG. 30 is a partial view of the center elliptical member according to one embodiment of this invention.
Figure 31:
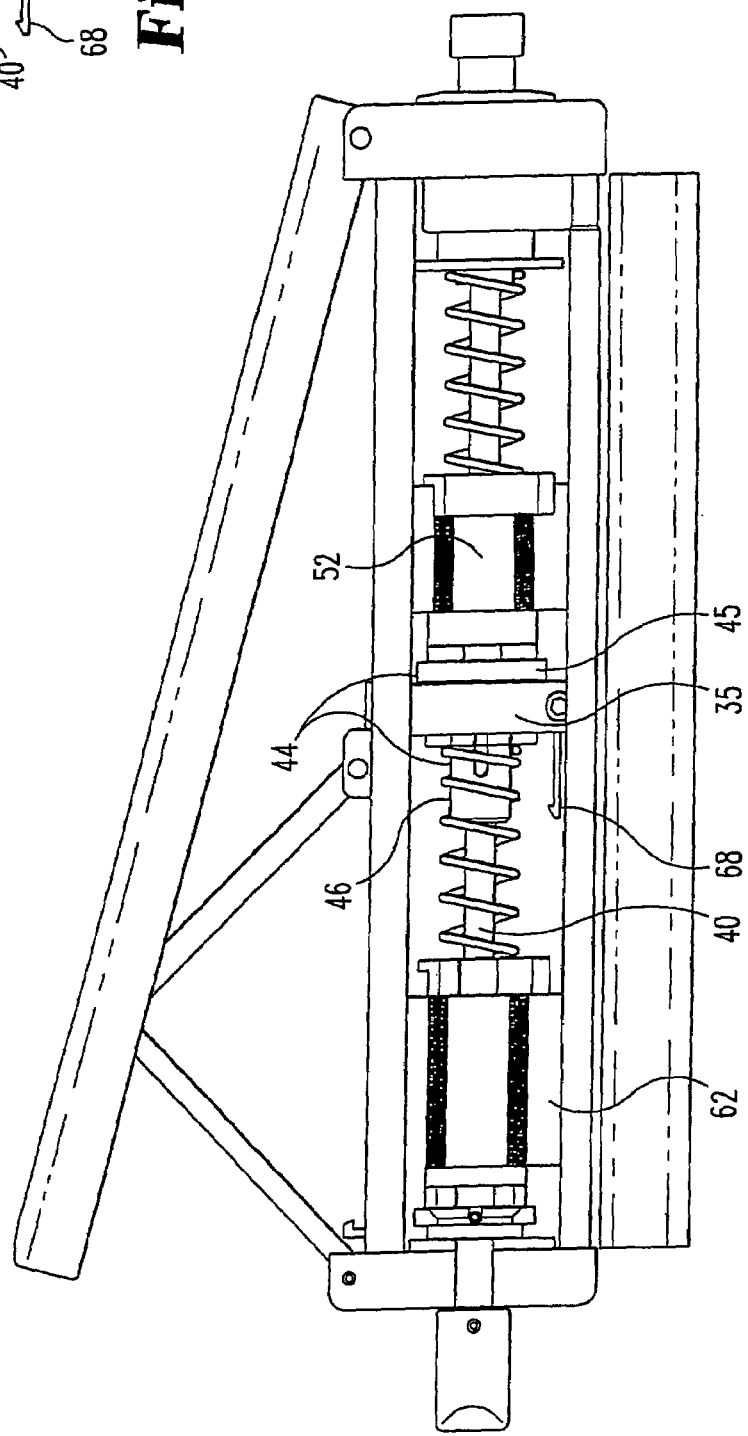
FIG. 31 is a side elevational view of the embodiment shown in FIG. 30.
Figure 32:
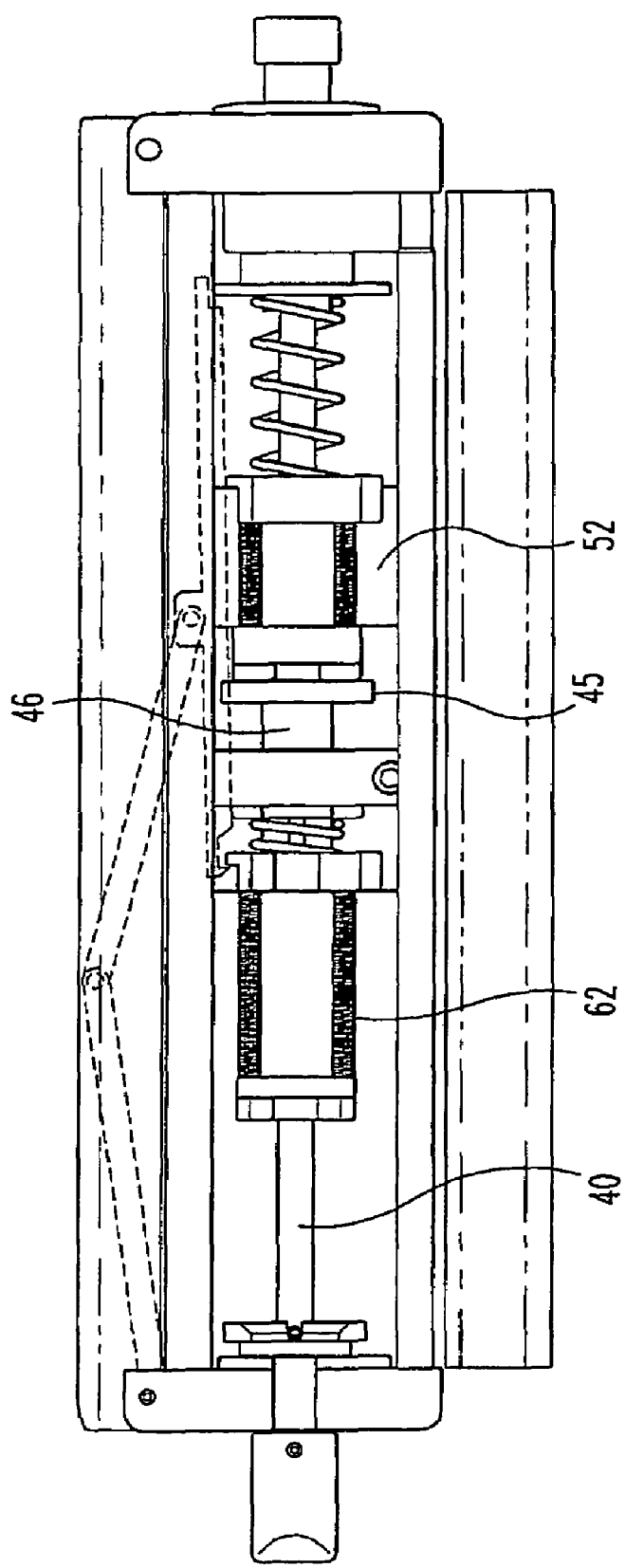
FIG. 32 is a side elevational view of the embodiment shown in FIG. 30.

In one embodiment shown in FIGS. 30-32, the forward retaining member 68 is disposed on the transverse wall 35. The center elliptical member 44 includes the center elliptical plate 45 and a tubular portion 46 coaxially aligned with the center shaft 40. The tubular portion 46 has a diameter greater than an outer diameter of the shaft 40. An internal spring 39 is disposed around the center shaft 40, as shown in FIG. 30, and acts between the tubular portion 46 and the forward carrier 62. The rearward carrier 52 is disposed against the center plate 45 when the rearward carrier 52 is in the resting position as shown in FIG. 31. When the forward carrier 62 is moved to the cocked position shown in FIG. 32, the internal spring 39 pushes the center elliptical member 44, which then acts upon the rear carrier 52 and pushes it to a staging position shown in FIG. 32. The rear carrier 52 is now optimally positioned to receive the rearward engagement member 97 of the cocking slider 90.

In another specific embodiment, a timing plate 160 is provided as shown in FIG. 20. The timing plate 160 helps maintain the slider 90 in proper position.

The sequence of events from the user's perspective is as follows. The user simply loads a needle set into the device 10 as is known in the art. The user then turns one of the safety knobs 130, 140 to cover the respective trigger button 105, 115. The other safety knob turns in unison. The cocking lever 70 is then unlocked and will spring outwardly upon application of slight pressure on the free end 71 of the cocking lever 70. The user cocks the gun by squeezing the cocking lever 70 so that it fully contacts the housing 20 of the device 10. The cocking lever 70 will again spring open, and the gun 10 can be fully cocked by squeezing the cocking lever 70 against the housing 20 of the gun 10. As the cocking lever 70 contacts the housing 20 of the gun 10 a second time, it will be latched and remain closed. The user than simply turns one of the safety knobs 130, 140 to expose the trigger buttons 105, 115, and depresses one of the trigger buttons 105, 115, and the gun fires.

In operation, the device 10 is at first in a resting state wherein the safety knobs 130, 140 are in an open position with the trigger buttons 105, 115 exposed, and the cocking lever 70 is latched in a closed position. When the safety knobs 130, 140 are open, the major axis of the front lever safety cam is perpendicular to the path of the lever latch. The major dimension of the front lever safety cam has a length sufficient to block passage of the lever latch along its path. Since the lever latch cannot move along its path, it cannot disengage the cocking lever hook. In this position, the rocker assembly is disposed within the recess of the cocking lever with the cocking beams extended against the bias of the cocking assembly spring.

When one safety is rotated to obstruct the corresponding trigger, the center shaft, the cams and the opposite safety knob are rotated. In one embodiment, the rear safety blocks movement of the rear trigger, which in turn prevents movement of the front trigger through the trigger link. Rotating one of the safety knobs in turn rotates the front lever safety cam to a position wherein the minor axis is perpendicular to the path of the lever latch. The minor dimension has a length that does not permit it to block the lever latch path, and the lever latch is free to move in a forward direction and disengage the cocking lever hook.

When the cocking lever 70 is released, the force transmission assembly operates to allow the cocking lever 70 to swing open a specific distance. As the cocking lever swings 70 open, the beam bearing 85 slides within the groove defined in the cocking lever and the cocking slider connector slides within its groove so that the cocking lever is in the open position. The cocking beams then are in their retracted position and the cocking slider is lined up to engage the cannula carrier. Depressing the cocking lever applies a force to the pivot point between the cocking beams. This force is transmitted along the inboard beam to depress the connector and the cocking slider so that the cocking slide hook captures a portion of the cannula carrier. Further depressing the cocking lever forces the cocking beams to the extended position. As the slider moves, it pulls the cannula carrier to the cocked position adjacent the center support where it is caught by the cannula carrier catch. As the line of action of the applied force changes (as the beams pivot), a linear force is applied to push the slider forward Since the cocking lever is biased to the open position, the cocking lever then swings open a second time. As the cocking lever swings open, the slider assembly pulls the cocking slider back to its starting position and disengage the cannula carrier. With the cannula carrier in its cocked position, a portion of the carrier bears against the slider causing it to pivot slightly so that the cocking slider is positioned with its pushing surface aligned with a surface of the stylet carrier. As the cocking lever is depressed, the connector pushes against the cocking slider causing it to translate until it engages the stylet carrier. Further pressure on the cocking lever forces the cocking beams to the extended position, which pushes the stylet carrier to the cocked position where it is caught by the stylet carrier catch.

When the stylet carrier travels to the cocked position, it contacts the cocking lever latch pusher, which is operatively connected to the lever latch through the lever latch link tube. The lever latch is moved to engage the locking lever hook, which holds the cocking lever in the closed position.

One of the safety knobs is then rotated to expose the triggers. This in turn rotates the opposite safety knob and the safety cams. The center and rear safety cams rotate so that the major axis intersects the cocking slider. The center and rear cams have a major dimension and a position such that they contact the cocking slider to push it towards the recess in the cocking lever so that both the cannula carriage and the stylet carriage are fully disengaged. The front lever safety cam is also rotated so that the major axis intersects the path of the lever latch. This locks the cocking lever in the closed position.

Depressing one of the triggers moves the stylet carrier catch to release the stylet carrier. The stylet carrier contacts the cannula carrier catch to release the cannula carrier. The two triggers are operatively connected by a trigger link shaft.

Other embodiments of the invention will be apparent to those skilled in the art from consideration of the specification and practice of the invention disclosed herein. It is intended that the specification, drawings and examples be considered as exemplary only, with the true scope and spirit of the invention being indicated by the following claims. It should be understood that only the preferred embodiments have been shown and described and that all changes and modifications that come within the spirit of the invention are desired to be protected.

What is claimed is:

1. An automatic tissue sampling apparatus for use with a biopsy needle set having an inner needle and an outer cannula, comprising:

an elongated housing having a forward end defining an opening for passage of the inner needle and outer cannula, said housing defining an interior cavity and configured to be held by an operator's hand along the length thereof;

a first carrier slidably disposed within said interior cavity and having a portion configured to support one of the inner needle and the outer cannula;

a second carrier slidably disposed within said interior cavity and having a portion configured to support the other of the inner needle and the outer cannula;

a first driving mechanism disposed within said interior cavity in operable engagement with said first carrier, said first driving mechanism having a cocked position in which said mechanism stores potential energy and a firing position in which said mechanism releases the potential energy to drive said first carrier toward said forward end of said housing;

a second driving mechanism disposed within said interior cavity in operable engagement with said second carrier, said second driving mechanism having a cocked position in which said mechanism stores potential energy and a firing position in which said mechanism releases the potential energy to drive said second carrier toward said forward end of said housing; and a cocking mechanism operable to sequentially move said first driving mechanism to its cocked position and said second driving mechanism to its cocked position, said cocking mechanism including a manually operated cocking lever positioned outside said housing for single handed manipulation by the same operator's hand holding said housing, wherein said cocking lever is pivotally supported on said housing, and includes a cocking slider having an engagement portion and an elongated bar slidably disposed within said housing so that when said cocking slider slides in a rearward direction away from said forward end of said housing said engagement portion applies a force against at least one of said first and second carriers to move the carrier to its cocked position, said engagement portion including a forward engagement member defined at a forward end of said bar arranged to engage said first carrier and a rearward engagement member arranged to engage said second carrier; and a force transmission mechanism engaged between said cocking lever and said cocking slider and configured to translate pivoting movement of said cocking lever to sliding movement of said cocking slider in said rearward direction against said at least one of said first and second carriers, said force transmission mechanism including a first elongated beam slidably supported at one end by said cocking lever and pivotally connected at an opposite end to said elongated bar, wherein said first elongated beam is pivotally connected at a position along the length of said elongated bar of said cocking slider closer to the forward end of said bar than to the rearward end of said bar.

2. The automatic tissue sampling apparatus of claim 1, wherein said forward engagement member defines a hook for engaging said first carrier to pull said first carrier as said cocking slider slides rearward.

3. The automatic tissue sampling apparatus of claim 2, wherein said rearward engagement member defines a notch for engaging said second carrier to push said second carrier as said cocking slider slides rearward.

4. The automatic tissue sampling apparatus of claim 1, wherein said rearward engagement member defines a notch for engaging said second carrier to push said second carrier as said cocking slider slides rearward.

5. An automatic tissue sampling apparatus for use with a biopsy needle set having an inner needle and an outer cannula, comprising:

an elongated housing having a forward end defining an opening for passage of the inner needle and outer cannula, said housing defining an interior cavity and configured to be held by an operator's hand along the length thereof;

a first carrier slidably disposed within said interior cavity and having a portion configured to support one of the inner needle and the outer cannula;

a second carrier slidably disposed within said interior cavity and having a portion configured to support the other of the inner needle and the outer cannula;

a first driving mechanism disposed within said interior cavity in operable engagement with said first carrier, said first driving mechanism having a cocked position in which said mechanism stores potential energy and a firing position in which said mechanism releases the potential energy to drive said first carrier toward said forward end of said housing;

a second driving mechanism disposed within said interior cavity in operable engagement with said second carrier, said second driving mechanism having a cocked position in which said mechanism stores potential energy and a firing position in which said mechanism releases the potential energy to drive said second carrier toward said forward end of said housing; and a cocking mechanism operable to sequentially move said first driving mechanism to its cocked position and said second driving mechanism to its cocked position, said cocking mechanism including a manually operated cocking lever positioned outside said housing for single handed manipulation by the same operator's hand holding said housing, wherein said cocking lever is pivotally supported on said housing, and includes a cocking slider having an engagement portion and an elongated bar slidably disposed within said housing so that when said cocking slider slides in a rearward direction away from said forward end of said housing said engagement portion applies a force against at least one of said first and second carriers to move the carrier to its cocked position, said engagement portion including a forward engagement member defined at a forward end of said bar arranged to engage said first carrier and a rearward engagement member arranged to engage said second carrier; and a force transmission mechanism engaged between said cocking lever and said cocking slider and configured to translate pivoting movement of said cocking lever to sliding movement of said cocking slider in said rearward direction against said at least one of said first and second carriers, said force transmission mechanism including;
  a first elongated beam slidably supported at one end by said cocking lever and pivotally connected at an opposite end to said elongated bar;
  a second elongated beam pivotally connected at one end to said housing; and
  a beam bearing pivotally connecting an opposite end of said second elongated beam to said one end of said first elongated beam, said beam bearing slidably supported by said cocking lever.

6. The automatic tissue sampling apparatus of claim 5, wherein said force transmission mechanism includes a biasing element at said one end of said second elongated beam operable to bias said second elongated beam away from said housing, whereby said second elongated beam pivots said cocking lever away from said housing as said second elongated beam pivots away from said housing.

7. The automatic tissue sampling apparatus of claim 5, wherein said forward engagement member defines a hook for engaging said first carrier to pull said first carrier as said cocking slider slides rearward.

8. The automatic tissue sampling apparatus of claim 7, wherein said rearward engagement member defines a notch for engaging said second carrier to push said second carrier as said cocking slider slides rearward.

9. The automatic tissue sampling apparatus of claim 5, wherein said rearward engagement member defines a notch for engaging said second carrier to push said second carrier as said cocking slider slides rearward.

10. An automatic tissue sampling apparatus for use with a biopsy needle set having an inner needle and an outer cannula, comprising:
  a housing having a forward end defining an opening for passage of the inner needle and outer cannula, said housing defining an interior cavity;
  a first carrier slidably disposed within said interior cavity of said housing and having a portion configured to support one of the inner needle and the outer cannula;
  a second carrier slidably disposed within said interior cavity and having a portion configured to support the other of the inner needle and the outer cannula;
  a first driving mechanism disposed within said interior cavity in operable engagement with said first carrier, said first driving mechanism including a first spring compressible to a cocked position to store potential energy and releasable from said cocked position to release the potential energy to drive said first carrier toward said forward end of said housing;
  a second driving mechanism disposed within said interior cavity in operable engagement with said second carrier, said second driving mechanism including a second spring compressible to a cocked position to store potential energy and releasable from said cocked position to release the potential energy to drive said second carrier toward said forward end of said housing; and
  a cocking mechanism operable to compress said first spring, said cocking mechanism including:
    a cocking lever positioned outside said housing and pivotally mounted to said housing to be manually depressed against the housing;
    a cocking slider having an engagement portion, said cocking slider slidably disposed within said housing so that when said cocking slider slides in a rearward direction away from said forward end of said housing said engagement portion applies a force against said first carrier to move the first carrier rearward; and
    a force transmission mechanism operably coupled between said cocking lever and said first carrier and configured so that the force required to manually depress said cocking lever to compress said first spring does not increase as said first spring is compressed, said force transmission mechanism including;
      a first elongated beam slidably supported at one end by said cocking lever and pivotally connected at an opposite end to said cocking slider;
      a second elongated beam pivotally connected at one end to said housing; and
      a beam bearing pivotally connecting an opposite end of said second elongated beam to said one end of said first elongated beam, said beam bearing slidably supported by said cocking lever.

* * * * *